US008801672B2

(12) United States Patent
Nagy et al.

(10) Patent No.: US 8,801,672 B2
(45) Date of Patent: Aug. 12, 2014

(54) PIVOTABLE NEEDLE PROTECTOR (75) Inventors: Antal Nagy, Hajduboszormeny (HU); Zoltan Gati, Devrecen (HU); Vilmos Perenyi, Debrecen (HU); Wolfgang Witt, Gelnhausen-Hailer (DE); Sandor Szilagyi, Debrecen (HU); Laszlo Juhasz, Debrecen (HU)

(73) Assignee: Dispomedicor Zrt., Debrecen (HU)

( * ) Notice: Subject to any disclaimer, the term of this patent is extended or adjusted under 35 U.S.C. 154(b) by 25 days.

(21) Appl. No.: 13/318,867

(22) PCT Filed: May 5, 2010

(86) PCT No.: PCT/HU2010/000049
§ 371 (c)(1),
(2), (4) Date: Nov. 4, 2011

(87) PCT Pub. No.: WO2010/128344
PCT Pub. Date: Nov. 11, 2010

(65) Prior Publication Data
US 2012/0046616 A1 Feb. 23, 2012

(30) Foreign Application Priority Data
May 6, 2009 (HU) .................................... 0900282

(51) Int. Cl.
*A61M 5/32* (2006.01)
(52) U.S. Cl.
USPC ........................................................ 604/192
(58) Field of Classification Search
USPC .................................. 604/192–198
See application file for complete search history.

(56) References Cited

U.S. PATENT DOCUMENTS

| 5,017,189 A | | 5/1991 | Boumendil |
| 5,139,489 A | * | 8/1992 | Hollister ........................ 604/192 |
| 5,490,841 A | | 2/1996 | Landis |
| 5,885,249 A | | 3/1999 | Irisawa |

FOREIGN PATENT DOCUMENTS

| EP | 0 381 577 A2 | 8/1990 |
| WO | WO 00/41749 A1 | 7/2000 |
| WO | WO 2007/110043 A1 | 10/2007 |

OTHER PUBLICATIONS

International Search Report of PCT/HU2010/000049 (Aug. 31, 2010).

* cited by examiner

*Primary Examiner* — Nicholas Lucchesi
*Assistant Examiner* — Pritesh Patel
(74) *Attorney, Agent, or Firm* — Millen, White, Zelano & Branigan, P.C.

(57) ABSTRACT

At the pivotable needle protector (1) according to the invention, the needle (2) is enveloped by a protective tube (3) with a slit on the side and pivotable around a hinge (5), the hinge (5) of the protective tube (3) is connected to an appendix (4) fixed on the part of the needle (2) toward the syringe, in the inside of the protective tube (3) there are valve elements (6) on both sides farthering from the slit (7), functioning as check valve regarding the movement of the needle (2). The solution is characterized by that, before the check valve at least one more valve is formed in the protective tube (3) in direct connection with the needle (2) when moving, preventing only the two-way movement of the needle (2) with the help of one or more flexible valve membranes (8) protruding from the wall of the protective tube (3).

20 Claims, 10 Drawing Sheets

PIVOTABLE NEEDLE PROTECTOR

Among the known solutions, the essence of the solution according to the US 2009/0018510 patent description is the following: the needle is protected by a protective tube of three parts, one element of the protective tube is a lid that can be torn off, placed on the slit of the needle protector, the other element is the protective tube itself, slit along its whole length, whereas the third element is a cylindrical part fixed to the needle joining the protective tube by a hinge. The protective tube is kept on its place before use by a joining mechanism placed on the opposite side of the hinge. After use, an additional, so-called second fixing mechanism starts working. This second fixing mechanism consists of clamps formed symmetrically in the inside of the protective tube, and among them, in the middle, there is a gap letting through the needle. Their formation allows the needle having gone through the gap to be fixed behind them.

The drawback of the solution is, that it consists of three parts, and a complicated joining element is needed on the opposite side of the hinge.

The US 2001/0004970 patent description is known as well, the essence of which is the following: the needle is protected by a protective tube, with a slit on its side, said protective tube can be unfolded around the hinge, and in the middle region of the tube there is a hook working as a check valve protruding into the gap open on the side, and when the needle is folded, it springs back above the needle. The needle protector connects on the syringe with snapping claws. After use the needle, the needle protector is snapped on the syringe and the protective tube is folded down on it from the side and is fixed with the hook.

The drawback of this solution is that before use there isn't any protection, because it ensures protection only after use when it is placed and turned up.

The US 2003/0212369 patent description is also known, the essence of which is the following: before use the needle is protected primarily by a closed needle protector, and secondary by a protective cap open on its side which can be unfolded around the hinge. In the inside of the protective cap there are ribs lengthwise next to each other, protruding from one side of the protective cap, keeping the needle in its place after turning up, preventing so the needle causing injuries. The protective cap can be made in one piece with the hinge.

The drawback of the solution is that before use only a distinct protective tube provides protection, and only after its removal is possible to turn up the protective element.

The US 2007/0265566 patent description is also known, the essence of which is the following: The needle can be protected by a needle protector open on the side, that can be rotated around a hinge, and said needle protector can be folded down on the needle after use. The fixing of the needle protector can take place in two ways: there is a claw clutch above the hinge, and there is a hook inside the needle protector and when the needle moves along it, then it springs back above the needle and fixes it.

The drawback of the solution is, that before use a separate protective tube provides protection only, and only after it was removed, the protective element can be installed and folded up.

The U.S. Pat. No. 5,139,489 patent description makes known a solution, the essence of which is the following: the needle can be protected by a needle protector open on the side, that can be pivoted around a hinge and it can be folded on the needle after use. Inside the needle protector there are two hooks opposite each other, and when the needle passes them, then they spring back above the needle and fix it. The needle is led into a slit elsewhere.

The drawback of the solution is, that before use only a separate protective tube provides protection and the protective element can be folded up after its removal.

Beside eliminating the deficiencies of the known solutions, we aimed to create a solution ensuring the protection of the needle while unpacking it, that is directly before use, on the other hand after use it could be definitively fixed having simply folded up the needle protector so ensuring constant protection without other disposable part. We realized that if the needle protector is provided with an element only preventing the needle in its movements, then the needle protector offers protection immediately after removing the packaging and on the other hand the needle can be used by simply unfolding the needle protector.

The set aim can be achieved by a needle protector, which can be pivoted on the side and where the needle is enveloped by a protective tube slit on its side, that can be pivoted around a hinge, and the hinge of the protective tube joins the appendix fixed to the needle close to the syringe, and inside the protective tube on two sides, farthering from the slit, there are valve elements touching with the needle directly, functioning as check valves regarding the movement of the needle. In case of the solution according to the invention we realized, that if there is at least one more valve in direct contact with the needle during its movement before the check valve in the protective tube, only preventing the two-way movement of the needle with the help of one or more flexible valve membrane protruding from the wall of the protective tube, then the set aim can be achieved.

The invention is a pivotable needle protector, where the needle is enveloped by a protective tube with a slit on the side and pivotable around a hinge, the hinge of the protective tube is connected to an appendix fixed on the part of the needle toward the syringe, in the inside of the protective tube there are valve elements on both sides farthering from the slit, functioning as check valve regarding the movement of the needle. The solution according to the invention is characterized by that, before the check valve at least one more valve is formed in the protective tube in direct connection with the needle when moving, preventing only the two-way movement of the needle with the help of one or more flexible valve membranes protruding from the wall of the protective tube.

In one preferred embodiment of the solution according to the invention, the protective tube is longer, than the needle and the cross section of the protruding part getting over the needle is of closed formation.

In another preferred embodiment of the solution according to the invention, one valve element of the valve elements functioning as check valve is shorter and is directed towards the side of the longer valve element and there is a gap between them, which is smaller, than the diameter of the needle.

In a further preferred embodiment of the solution according to the invention, the valve membrane is formed protruding from the edge of the slit of the protective tube and in the slit of the protective tube there are placed three valve membranes, one of them protrudes from one rim of the slit and the other two protrude from the other rim of it.

In a further preferred embodiment of the solution according to the invention, the valve membrane protrudes from one rim of the slit and ends close to the other rim.

In a further preferred embodiment of the solution according to the invention, the valve membrane is formed in one piece along 5-80% length of the slit.

In a further preferred embodiment of the solution according to the invention, the valve membrane is a projection inside the protective tube, protruding from one side of that, which is capable of pivoting to both direction under force, the flexible part of which is formed overhanging the axle of the slit, parallel with the slit, or farthering from it.

In a further preferred embodiment of the solution according to the invention, one of the valve elements functioning as check valve, is formed as a two-pronged projection, molded together with the valve membrane.

In a further preferred embodiment of the solution according to the invention, one of the valve elements functioning as check valve, is of rigid formation and there is formed a nest in it, housing the other valve element.

In a further preferred embodiment of the solution according to the invention, the gap between the valve elements functioning as check valve, is formed perpendicular to the direction of the slit.

In a further preferred embodiment of the solution according to the invention, the hinge is a so-called springing hinge with three parts, having a springing tensioning strap beside the eccentric knuckles, which is formed to hold the protective tube in extreme positions.

In a further preferred embodiment of the solution according to the invention, the hinge is a so-called ribbon hinge, which is made in closed position, and below and above it there are interlocking unfolding fixing cams, fixing the protective tube in down folded position.

In a further preferred embodiment of the solution according to the invention, the hinge is a so-called ribbon hinge, below which there is a unfolding fixing cam, formed in such a way, that it ensures temporary engagement to the coupling opening formed in the protective tube fixing the protective tube in down folded position.

In a further preferred embodiment of the solution according to the invention, the hinge is such a ribbon hinge, that is made in open position.

In a further preferred embodiment of the solution according to the invention, there is a tearing element confirming the first use, formed between the edges of the slit of the protective tube and the appendix.

In a further preferred embodiment of the solution according to the invention, the needle protector is provided with a further valve realized with compressible closing elements, joining the edges of the slit compressing and closing it.

In a further preferred embodiment of the solution according to the invention, the needle protector is provided with a further valve, realized in the form of a protective cap, which connects to the protruding part with the help of fixing elements preventing backward movement in pushed position movable in axial direction.

In a further preferred embodiment of the solution according to the invention, the raw material of the whole needle protector is flexible plastic.

In a further preferred embodiment of the solution according to the invention, the needle together with the needle protector is provided with sterilizable packaging.

The solution according to the invention is set forth by the enclosed figures:

The FIG. 1 shows the needle protector with the needle behind the first valve in perspective view.

The FIG. 2 shows the needle protector with the needle behind the return/check valve in perspective view.

The FIG. 3 shows the needle protector with the needle behind the first valve in section.

The FIG. 4 shows the needle protector according to the FIG. 3 with another hinge embodiment.

The FIG. 5 shows a different enlargement A-A section of the FIG. 3.

The FIG. 6 shows a different enlargement B-B section of the FIG. 3.

The FIG. 7 shows another version of the invention with fixed unfolding.

The FIG. 8 shows the enlarged C-C section of the FIG. 7.

The FIG. 9 shows the solution according to the invention with a first valve of different embodiment.

The FIG. 10 shows a different enlargement B-B section of the FIG. 3 with a different embodiment of the tube valve.

The FIG. 11 shows an supplemented version of the solution according to the invention.

The FIG. 12 shows the D-D section of the FIG. 11.

The FIG. 13 shows the pivoted and fixed version of the FIG. 11.

The FIG. 14 shows another version of the needle protector provided with closing elements that can be snapped together in perspective view.

The FIG. 15 shows the E-E section of the FIG. 14 with enlarged details of the closing elements and with a new valve membrane—valve element combination.

The FIG. 16 shows the F-F section of the FIG. 14 with another new version of valve membrane-valve element combination.

The FIG. 17 shows the F-F section of the FIG. 14 with a further new version of valve membrane-valve-element combination.

Figure 1:
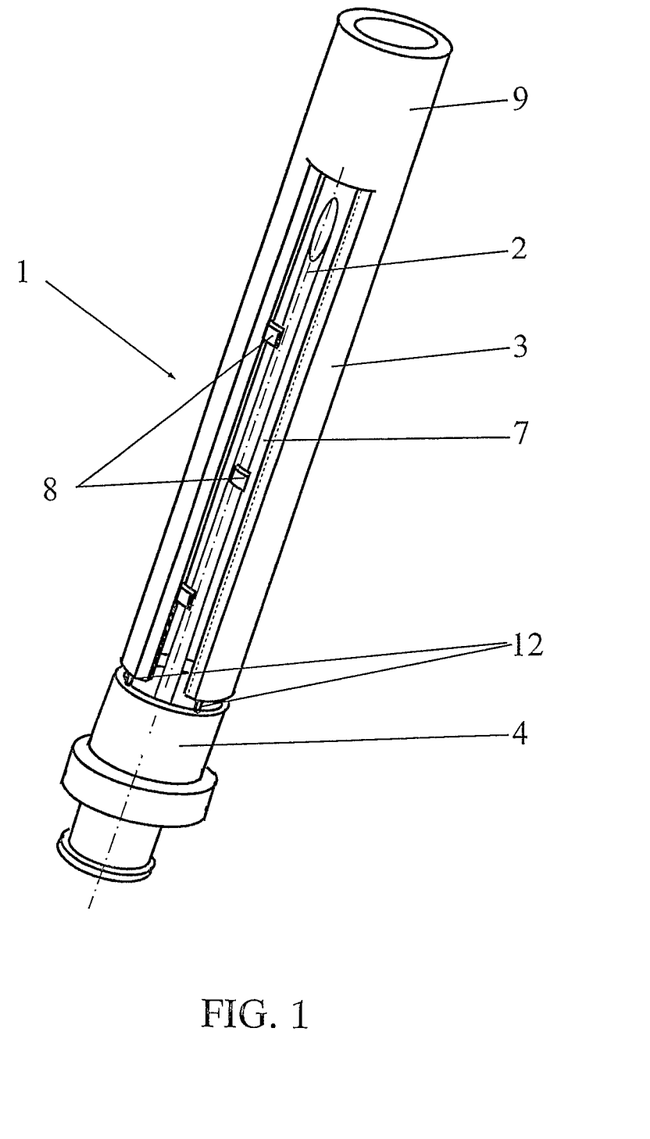

The FIG. 1 shows the needle protector with the needle behind the first valve in perspective view. The FIG. 1 shows in perspective view the formation of the first valve regarding the movement of the needle 2. In the slit 7 of the protective tube 3 there are valve membranes 8 serving as obstacles in the way of the movement of the needle 2. The slit 7 goes downward along the whole length of the protective tube 3. The valve membranes 8 are formed from one edge of the slit 7 toward the other edge, following the arch of the protective tube 3, between the ends of which there is a gap smaller, than the needle 2. So they only form an obstacle against the buckling of the needle 2, but resulting from an outside force make possible the two-way movement of the needle 2. In the figure there are three pieces of valve membrane 8, two of which is on one side of the slit 7, and one on the other side. These valve membranes 8 keep the needle 2 in the protective tube 3 before the use.

The needle protector 1 has two main parts: the protective tube 3 and the appendix 4. There is a tearing element 12 each connecting the lower edges of the slit 7 and the appendix 4. The intactness of these tearing elements 12 confirms that the needle 2 has not been used yet. During use against them with the breaking of the tearing elements 12 using outside force the protective tube 3 can be folded down and the needle 2 made ready for injecting.

A hinge 5 connects the protective tube 3 with the appendix 4. The appendix 4 is fixed to the lower part of the needle 2 joining the syringe. The protective tube 3 is longer, than the needle 2 to prevent causing injury by the needle 2 when folding down the needle 2 by grasping the needle protector 1 here, and it ensures as well the formkeeping of the slit 7. This protruding part 9 is concentrically closed in cross-section.

Figure 2:
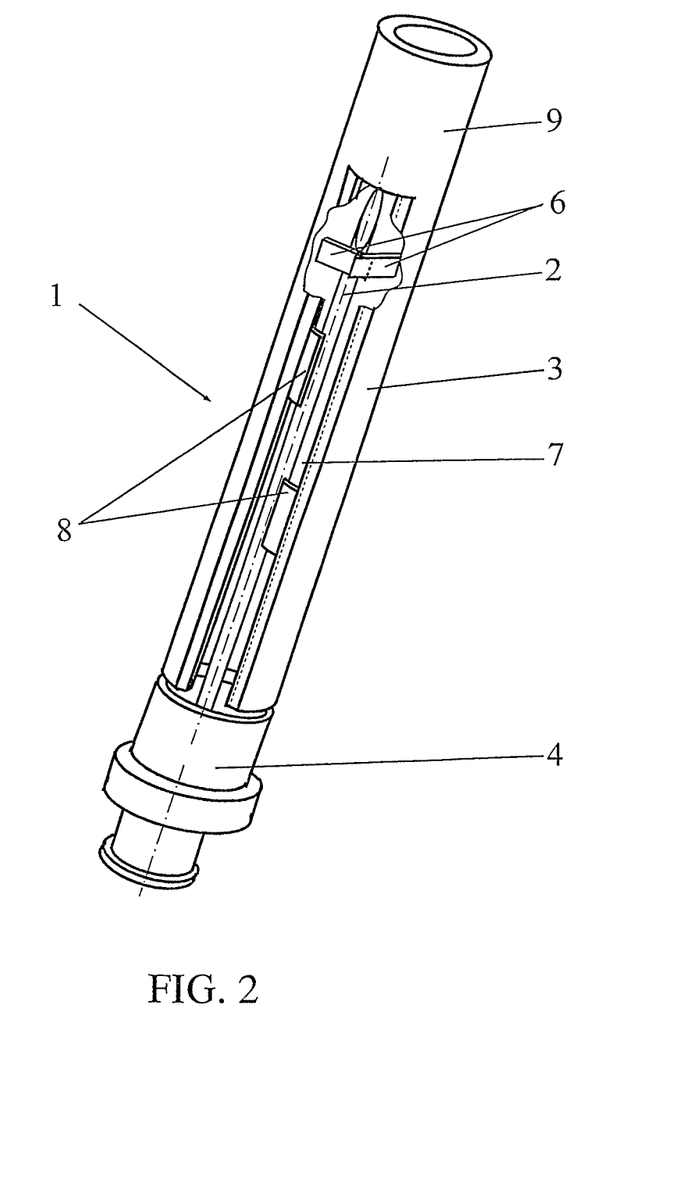

The FIG. 2 shows the simplest embodiment of the needle protector 1 with the needle 2 behind the valve elements 6 functioning as check valve in perspective view. The role of the valve elements 6 is to keep the needle 2 in the protective tube 3 snapping it behind the valve elements 6 after use. According to the example their formation is like this: they lie on two sides opposite the slit 7 from the inner wall of the protective tube 3 and between them there is a gap with a diameter smaller than that of the needle 2. (see the FIG. 5 as well). One valve element 6 of the valve elements 6 is shorter and is directed to the side of the longer valve element 6. Here the valve membranes 8 can be seen in another possible embodiment. Here on each side a longer valve membrane 8 is placed demonstrating, that such a formation also fits for the aim. It is also possible to form a valve membrane 8 protruding from one side, ending near the slit 7 (not shown in the figure), their length can be 5-80% of the length of the slit 7.

Figure 3:
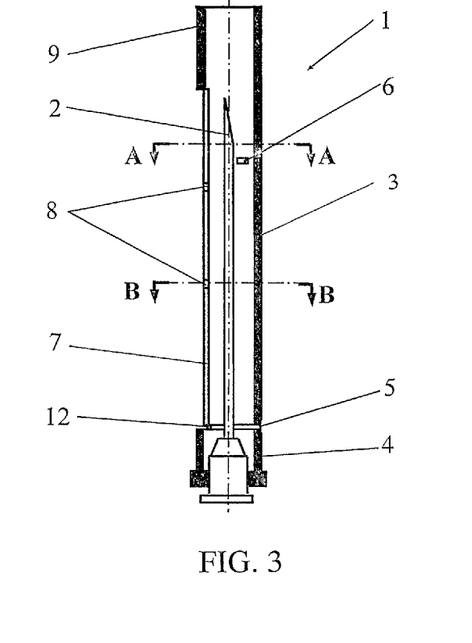

The FIG. 3 shows the needle protector 1 with the needle behind the first valve in section. It can be seen well, that the needle 2 is in its position before use, behind the valve membranes 8 forming the first valve, but in front of the valve elements 6. The tearing element 12 confirming the first use, connecting the lower edges of the slit 7 and the appendix 4 can be seen here as well. In this figure a simple, ribbon hinge (5) is depicted.

Figure 4:
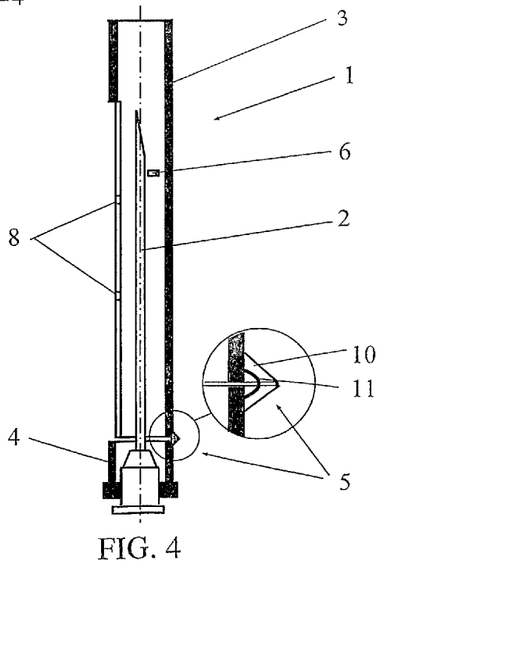

The FIG. 4 shows the needle protector according to the FIG. 3 with a another embodiment hinge, the formation can be seen in the enlarged part. Here a hinge 5 developed for beverage bottle caps and applied often is depicted, which has two knuckles 10 with a tensioning strap 11 between them. This tensioning strap 11 keeps the protective tube 3 in a downfolded position so during injection the protective tube 3 does not cause problems.

Figure 5:
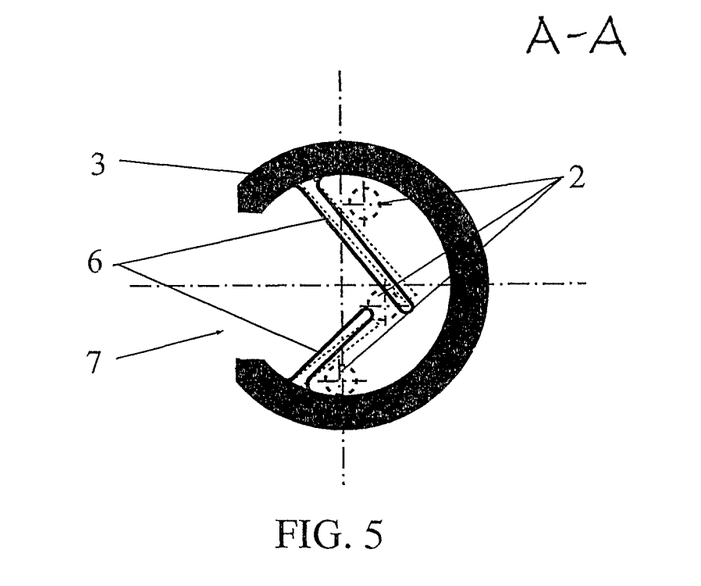

The FIG. 5 shows an enlarged size A-A section of the FIG. 3. The special formation of the valve elements 6 forming a check valve regarding the movement of the needle 2 can be seen well. The needle 2 is depicted in different positions to make observation of the function easier. After use the needle 2 gets behind the valve elements 6 having been led among them with force, and it is kept definitively in the protective tube 3. The movement of the valve elements 6 during function is depicted by a dashed line.

Figure 6:
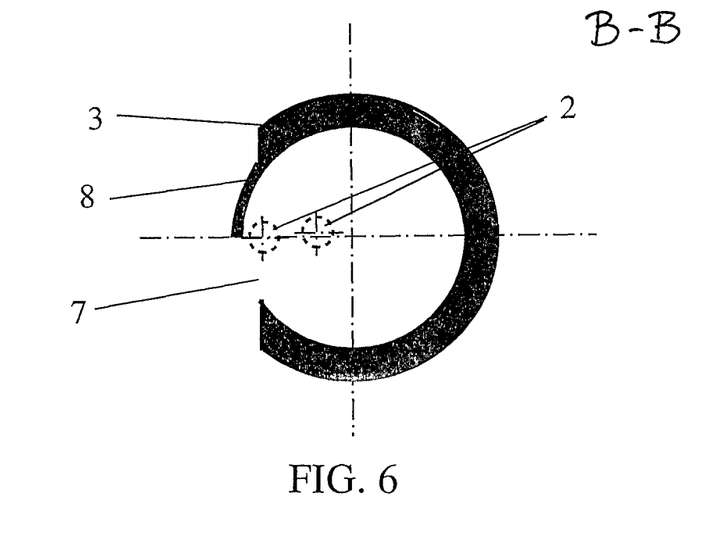

The FIG. 6 shows the B-B section of the FIG. 3, also enlarged, showing one of the preferable embodiment of the valve membranes 8. Their thin, membrane-like formation makes possible the leading of the needle 2 into the protective tube 3, but resulting from force the needle 2 can be lifted out of them. The gap between them is smaller, than the outer diameter of the needle 2. The valve membranes 8 protrude preferably into the slit 7 in such a way, that they follow the shape of the protective tube 3, but their thickness is considerably smaller, than that of the protective tube 3. Here the needle 2 was shown during movement as well.

Figure 7:
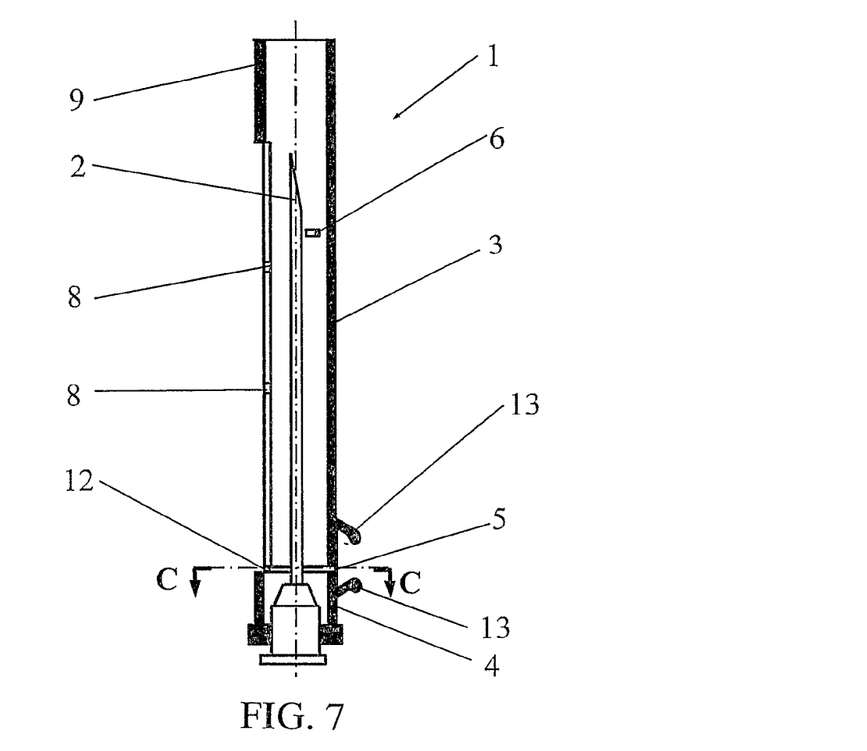

The FIG. 7 shows another version of the invention with fixed unfolding, where below and above the ribbon hinge 5 an unfolding fixing cam 13 is placed. These grasp each other during the complete down-folding of the needle protector 1 and fix the protective tube 3 in folded out position. The unfolding fixing cams 13 are parallel with the ribbon of the hinge 5.

Figure 8:
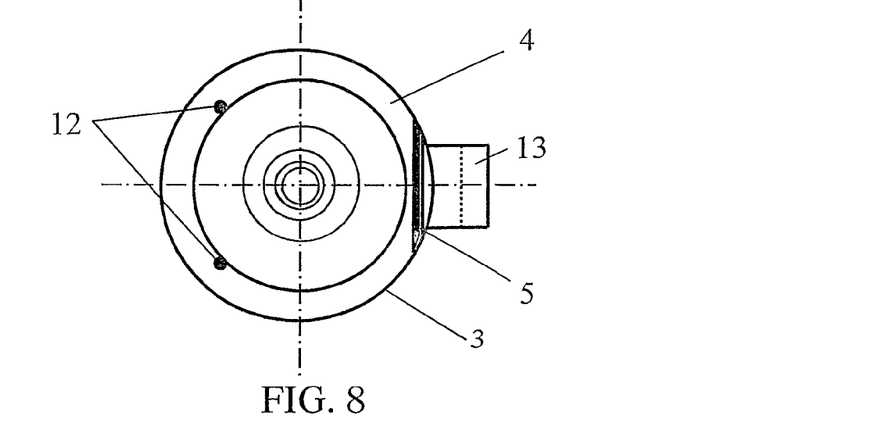

The FIG. 8 shows the enlarged C-C section of the FIG. 7. Here the formation and position of a so-called ribbon hinge 5 and the tearing element 12 can be seen well. The unfolding fixing cam 13 in top view can be seen below the hinge 5 (the connecting plane is depicted with dashed line).

Figure 9:
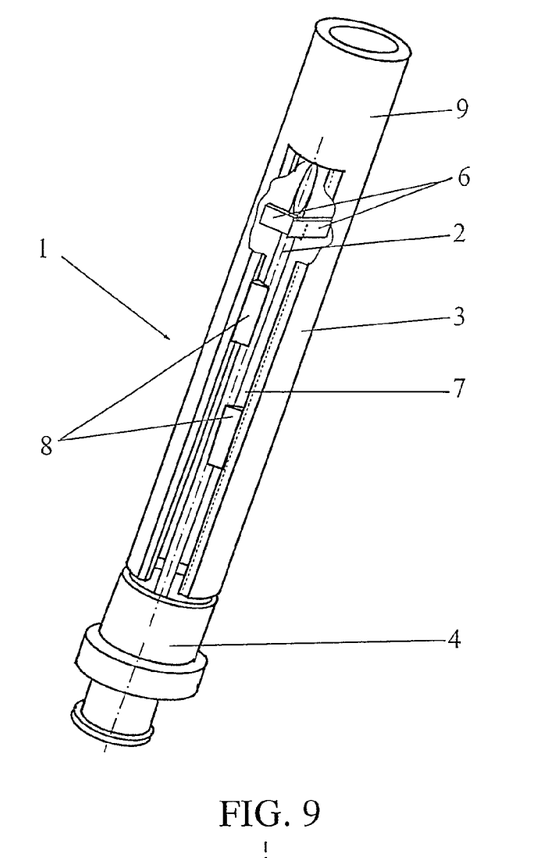
Figure 10:
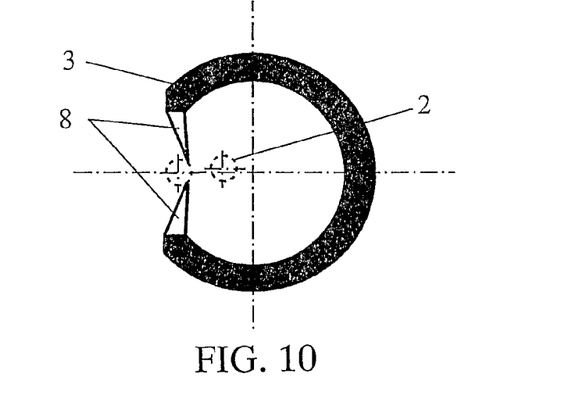

The FIGS. 9 and 10 show the invention with a first valve of different embodiment. Here the valve membranes 8 are of thinning formation towards its edges and they are directed towards the inside of the protective tube 3. This embodiment ensures the keeping of the needle 2 in a deeper position.

Figure 11:
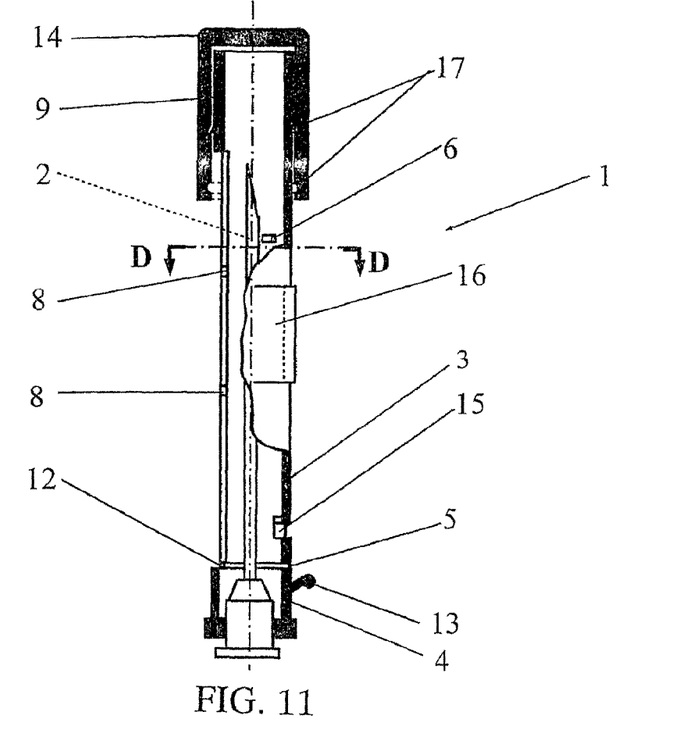

The FIG. 11 shows an other version of the invention supplemented with a protective cap 14. The safer keeping of the needle 2 in the protective tube 3 can be ensured by a protective cap 14 functioning as an additional valve. The protective cap 14 is fixed in an axial direction in a mobile way to the protruding part 9 of the protective tube 3. The protective cap 14 is kept on its place by fixing elements 17. These elements are formed in such a way, that they make possible the removal of the protective cap 14 in their position before use, but after use they do not allow it. It is ensured by forming protrusions of saw-tooth section, or a ring is formed on the protruding part 9 whereas in the inside of the protective cap 14 a saw-tooth like formation matching the previous ones and an arch-like groove at the rim is formed. This formation makes possible the removal of the protective cap 14 before use, but if it is pressed after use, fixing the needle 2 this way, then the removal of the protective cap 14 is not possible any more. The protective cap 14 is shown in this pressed position. Another, safer possibility of grasping the protective tube 3 is also shown in this figure. At around the middle region of the protective tube 3 on the opposite side of the slit 7 a handle 16 with protruding rim is formed. This way the protective tube 3 should not be moved by grasping the protective cap 14, so the protective cap 14 must be caught only after use and pressing to fix the needle 2.

This figure shows another fixing method keeping the protective tube 3 in outfolded position. In this embodiment version only one unfolding fixing cam 13 is formed below the hinge 5 which snaps into the coupling opening 15 formed in the protective tube 3, when the protective tube 3 is folded down and fixes it in unfolded position (see the FIG. 13 as well).

Figure 12:
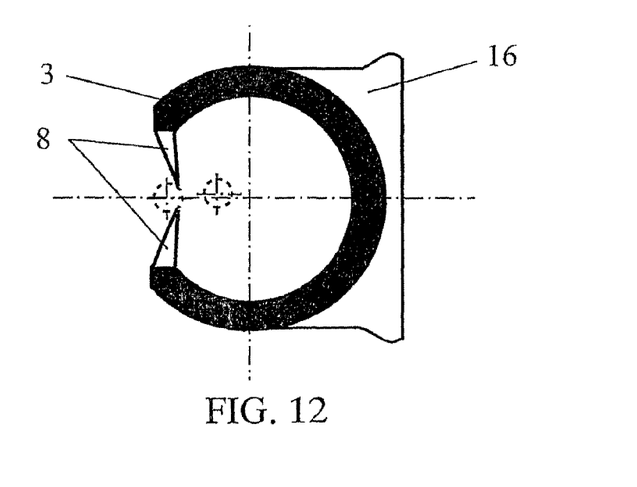

The FIG. 12 shows the D-D section of the FIG. 11 with the preferable formation of the handle 16 from the other side.

Figure 13:
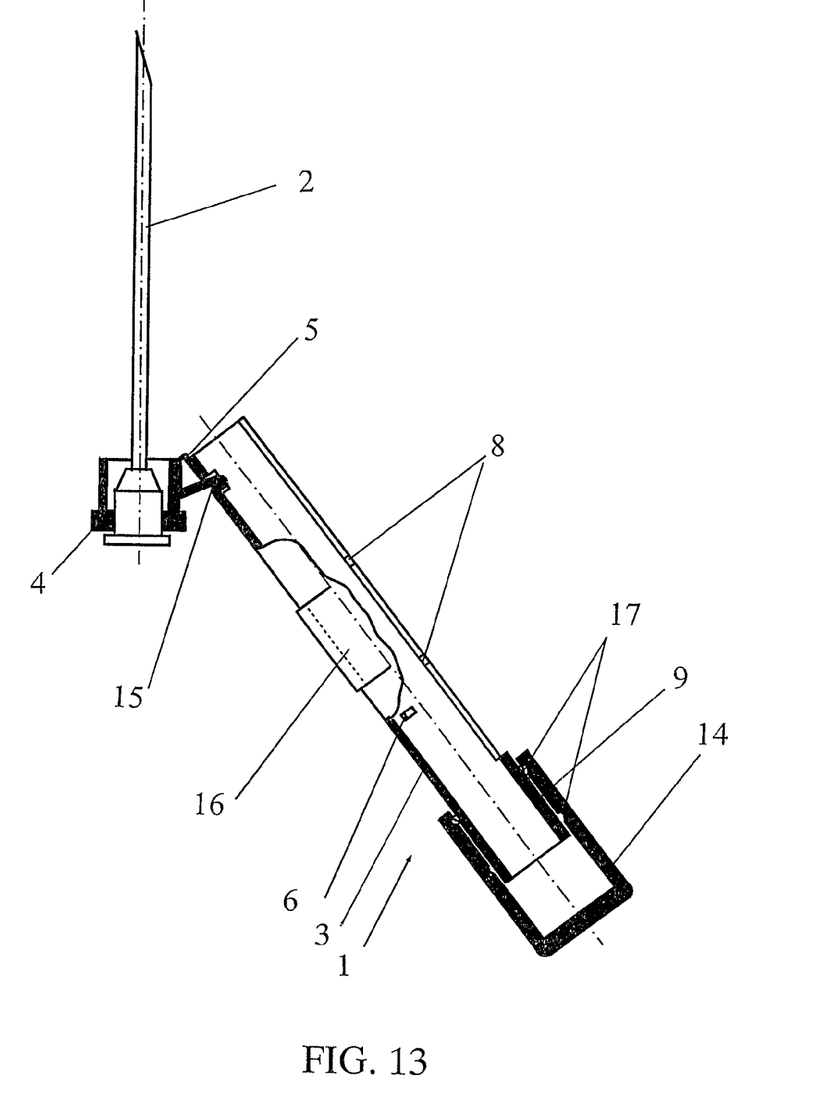

The FIG. 13 shows the pivoted and fixed version of the protective tube 3 with the fixing method described above. Here it can be seen well, that the unfolding fixing cam 13 fixes the protective tube 3 by springing into the coupling opening 15. The unfolding-fixing cam 13 and the coupling opening 15 is formed in such a way, that they are released each other resulting from force making possible the folding back of the protective tube 3 after use. The protective cap 14 can be seen in its starting position in the figure.

Figure 14:
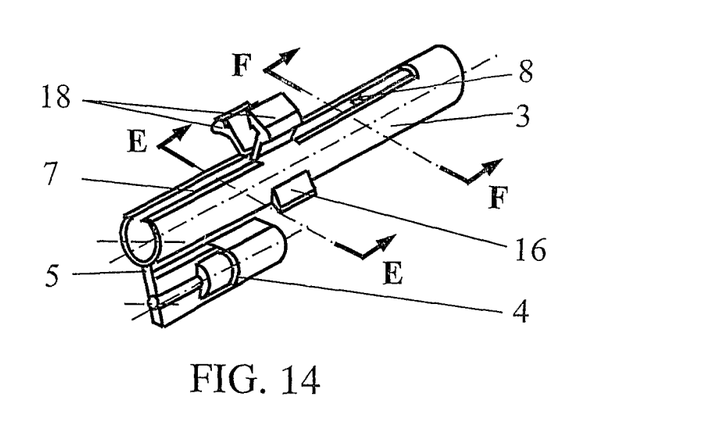

The needle protector 1 is shown in outfolded, manufacturing position in the FIG. 14. The hinge 5 of the protective tube 3 produced such a way tries to place itself in the manufacturing position resulting from the recollecting characteristic of plastics, so induces the protective tube 3 into an outfolded state. So to achieve ready to use state only the needle 2 has to be freed from the protective tube 3 against the valve membrane 8, and the hinge 5 drives the protective tube 3 into folded state and keeps it there, so it is unnecessary to keep this situation with the help of fixing elements 17. A further safety fix is depicted in the slit 7, which can be snapped together from closing elements 18, that cannot be decoupled after having been pressed by hand, so the needle 2 remains closed definitely in the protective tube 3. (The enlarged details are shown in the FIG. 15.)

The shown appendix 4 of the needle protector 1 is produced so, that it is molded directly together with the needle 2, so it can be immediately placed on the syringe.

Figure 15:
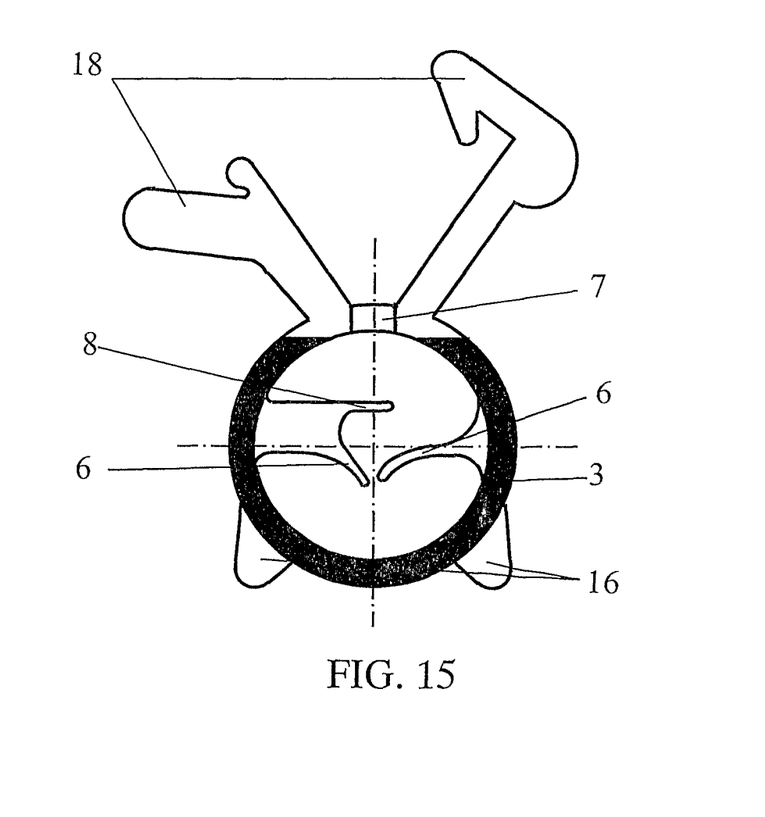

In the FIG. 15 besides the above mentioned formation of the closing elements 18, a new valve membrane—valve element combination is depicted, where one of the valve elements 6 of the check valve is produced by molding together with the valve membrane 8 of the first valve. This case there is one piece of the valve membrane 8, starting from the wall of the protective tube 3, protruding its mid-line, preventing the release of the needle 2 from the protective tube 3. The plane of the valve membrane 8 is here parallel with the plane of the slit 7. Both valve elements 6 of the check valve is formed here with a slight downward slope and the gap between them is smaller than the diameter of the needle 2.

Figure 16:
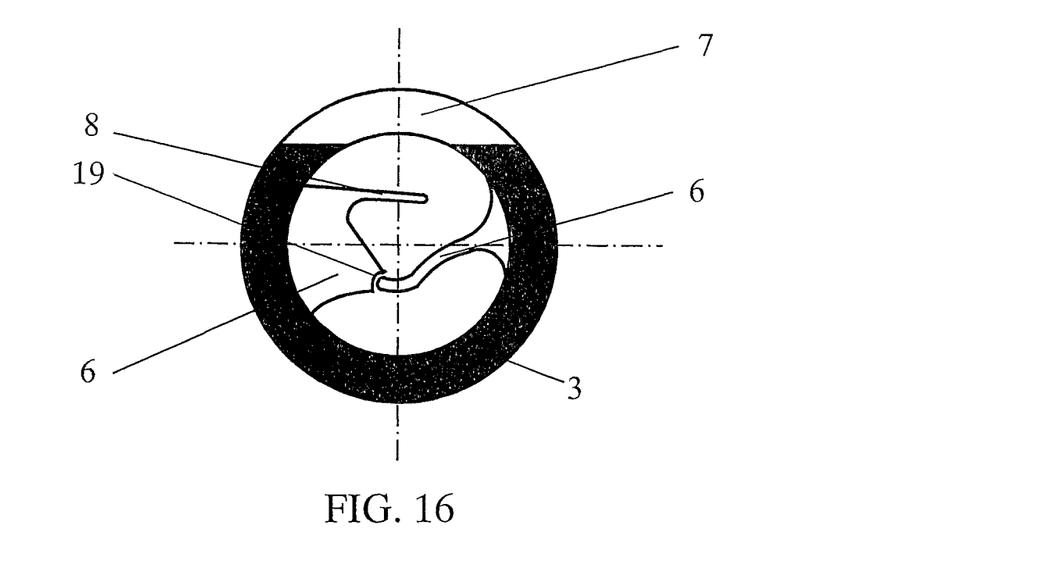

The FIG. 16 shows a new embodiment of valve membrane 8 and valve element 6. Here the valve element 6 is of rigid shape, molded together with the valve membrane 8. The other flexible piece of the valve element 6 is formed curved upwards at the end and housing into the nest 19 formed in the rigid pair on the opposite side, preventing perfectly the upward movement of the flexible valve element 6, by this the disengagement of the needle 2. The plane of the valve element 8 goes farthering from the slit 7 to prevent even more the accidental disengagement of the needle 2.

Figure 17:
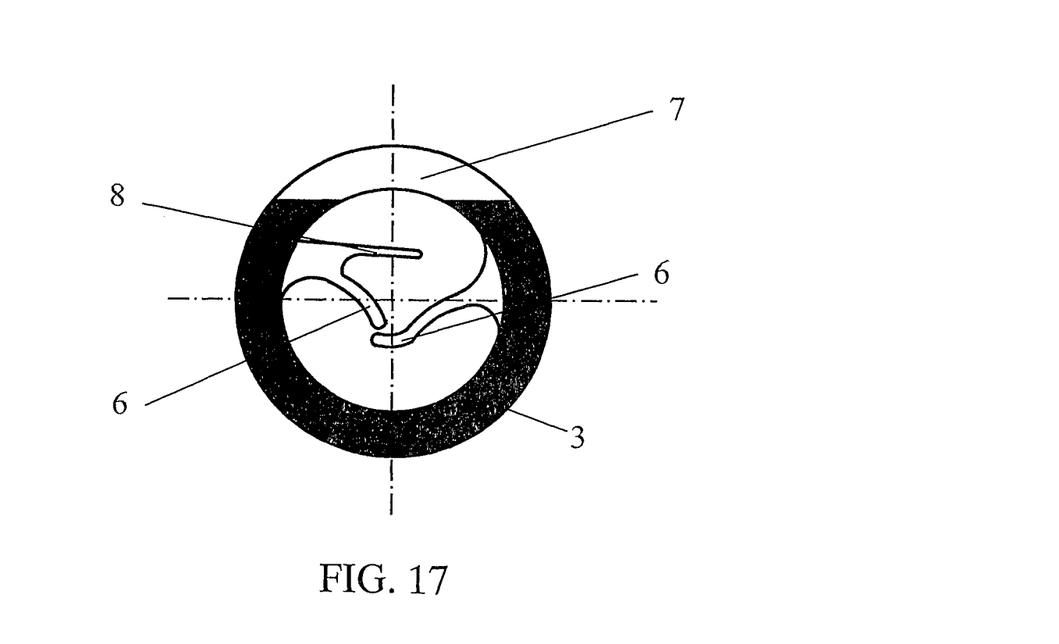

The FIG. 17 shows again another version of valve membrane-valve element combination, where all of the valve elements 6 are flexible and the gap between them promotes the lateral movement of the needle 2, but makes difficult the accidental spring of the needle 2. The advantage of this solution is, that in case the user wants to prepare the needle 2 for the first use, but accidentally moves the needle 2 to the wrong direction, then feeling the greater resistance can correct, and it is not necessary to throw away the unused needle 2.

The whole needle protector 1 can be preferably sterilized, or it can be marketed in sterile packaging.

In case of a possible preferable application of the needle protector according to the invention, the use of the simplest version of the needle protector takes place in such a way, that after removing the sterile packaging, the protective tube 3 is pivoted against the valve membranes 8 of the so-called first valve by applying mild force. In one version the hinges 5 help keep the pivoted state resulting in the ready to use state of the needle 2. In another version the protective tube 3 is fixed by the unfolding fixing cams 13. After the use the protective tube 3 is folded back through the first valve in such a way, that the needle 2 is definitely fixed on the bottom of the protective tube 3 by making it spring between the valve elements 6 of the check valve in the inside of the protective tube 3.

In case of a more improved version there is a tearing element 12 connecting the lower edges of the slit 7 and the appendix 4 showing first use and it should be torn when first used. In case of the modified version with protective cap and the version with snapping possibility, after the full folding back of the needle 2, the protective cap 14 must be pressed till impact, or the closing elements 18 should be snapped together, this way the storage of the used needle 2 is completely safe, it is not possible to use it again.

In case of a preferable embodiment, the needle 2 is pivoted to the right at angle 30-45° in the safety protective tube 3 for the sake of ergonomic formation compared to the direction of unfolding. The purpose of this rotation is, that after use the protective tube 3 can be closed back only with "one" hand, with the thumb, holding the syringe. Assuming that the user is right-handed and the syringe is held in their right hand during use. With turning the needle 2 to the right in case of a right-handed user the protective tube 3 gets to the left side compared to the vertical axle.

The advantageous effects of the invention manifest in that, we solved with the double valve system, that the needle protector 1 consist of few spare parts only, and it ensures safety even before use, and during unpacking, but the needle 2 be prepared easily for use. After use with an effective fixing it ensures definite protection against injuries and prevents reuse as well.

List of References:
1—needle protector
2—needle
3—protective tube
4—appendix
5—hinge
6—valve element
7—slit
8—valve membrane
9—protruding part
10—knuckle
11—tensioning strap
12—tearing element
13—unfolding fixing cam
14—protective cap
15—coupling opening
16—handle
17—fixing element
18—closing element
19—nest

The invention claimed is:

1. A pivotable needle protector, wherein the needle is enveloped by a protective tube with a slit on the side and pivotable around a hinge, the hinge of the protective tube is connected to an appendix fixed on the part of the needle toward the syringe, in the inside of the protective tube there are valve elements on both sides away from the slit, functioning as check valve regarding the movement of the needle,
wherein the check valve consist of two valve elements (6), one of the valve element (6) is a longer slab, and the other valve element (6) is shorter slab, which are elongated from the inner surface of the protective tube (3), and the two valve elements (6) are nearly perpendicular to each other, and there is a gap between the slab edge of the shorter valve element (6) and the slab surface of the longer valve element (6), which gap is smaller than the diameter of the needle (2), and
wherein before the check valve, at least one more valve is formed in the protective tube (3) in direct connection with the needle (2) when moving, preventing only the two-way movement of the needle (2) with the help of one or more flexible valve membranes (8) protruding from the wall of the protective tube (3).

2. The needle protector of claim 1, wherein the protective tube (3) is longer, than the needle (2) and the cross section of the protruding part (9) getting over the needle (2) is of closed formation.

3. The needle protector of claim 1, wherein the valve membrane (8) is formed protruding from the edge of the slit (7) of the protective tube (3) and in the slit (7) of the protective tube (3) there are placed three valve membranes (8), one of them protrudes from one rim of the slit (7) and the other two protrude from the other rim of it.

4. The needle protector of claim 1, wherein the valve membrane (8) protrudes from one rim of the slit (7) and ends close to the other rim.

5. The needle protector of claim 4, wherein the valve membrane (8) is formed in one piece along 5-80% length of the slit (7).

6. The needle protector of claim 1, wherein the valve membrane (8) is a projection inside the protective tube (3), protruding from one side of that, which is capable of pivoting to both direction under force, the flexible part of which is formed overhanging the axle of the slit (7), parallel with the slit (7), or away from it.

7. The needle protector of claim 1, wherein the gap between the valve elements (6) functioning as check valve, is formed perpendicular to the direction of the slit (7).

8. The needle protector of claim 1, wherein the hinge (5) is a so-called springing hinge with three parts, having a springing tensioning strap (11) beside the eccentric knuckles (10), which is formed to hold the protective tube (3) in extreme positions.

9. The needle protector of claim 1, wherein the hinge (5) is a so-called ribbon hinge, which is made in closed position, and below and above it there are interlocking unfolding fixing cams (13), fixing the protective tube (3) in down folded position.

10. The needle protector of claim 1, wherein the hinge (5) is a so-called ribbon hinge, below which there is a unfolding fixing cam (13), formed in such a way, that it ensures temporary engagement to the coupling opening (15) formed in the protective tube (3) fixing the protective tube (3) in down folded position.

11. The needle protector of claim 1, wherein the hinge (5) is such a ribbon hinge, that is made in open position.

12. The needle protector of claim 1, wherein there is a tearing element (12) confirming the first use, formed between the edges of the slit (7) of the protective tube (3) and the appendix (4).

13. The needle protector of claim 1, wherein the needle protector (1) is provided with a further valve realized with compressible closing elements (18), joining the edges of the slit (7) compressing and closing it.

14. The needle protector of claim 1, wherein the needle protector (1) is provided with a further valve, realized in the form of a protective cap (14), which connects to the protruding part (9) with the help of fixing elements (17) preventing backward movement in pushed position movable in axial direction.

15. The needle protector of claim 1, wherein the raw material of the whole needle protector (1) is flexible plastic.

16. The needle protector of claim 1, wherein the needle (2) together with the needle protector (1) is provided with sterilizable packaging.

17. A pivotable needle protector, wherein the needle is enveloped by a protective tube with a slit on the side and pivotable around a hinge, the hinge of the protective tube is connected to an appendix fixed on the part of the needle toward the syringe, in the inside of the protective tube there are valve elements on both sides away from the slit, functioning as check valve regarding the movement of the needle, wherein before the check valve, at least one more valve is formed in the protective tube (3) in direct connection with the needle (2) when moving, preventing only the two-way movement of the needle (2) with the help of one or more flexible valve membranes (8) protruding from the wall of the protective tube (3), wherein at least one of the following conditions A)-Q) is met
  A) one valve element (6) of the valve elements (6) functioning as check valve is shorter and is directed towards the side of the longer valve element (6) and there is a gap between them, which is smaller, than the diameter of the needle (2);
  B) the valve membrane (8) is formed protruding from the edge of the slit (7) of the protective tube (3) and in the slit (7) of the protective tube (3) there are placed three valve membranes (8), one of them protrudes from one rim of the slit (7) and the other two protrude from the other rim of it;
  C) the valve membrane (8) protrudes from one rim of the slit (7) and ends close to the other rim;
  D) the valve membrane (8) is formed in one piece along 5-80% length of the slit (7);
  E) the valve membrane (8) is a projection inside the protective tube (3), protruding from one side of that, which is capable of pivoting to both direction under force, the flexible part of which is formed overhanging the axle of the slit (7), parallel with the slit (7), or away from it;
  F) one of the valve elements (6) functioning as check valve, is formed as a two-pronged projection, molded together with the valve membrane (8);
  G) one of the valve elements (6) functioning as check valve, is of rigid formation and there is formed a nest (19) in it, housing the other valve element (6);
  H) the gap between the valve elements (6) functioning as check valve, is formed perpendicular to the direction of the slit (7);
  I) the hinge (5) is a so-called springing hinge with three parts, having a springing tensioning strap (11) beside the eccentric knuckles (10), which is formed to hold the protective tube (3) in extreme positions;
  J) the hinge (5) is a so-called ribbon hinge, which is made in closed position, and below and above it there are interlocking unfolding fixing cams (13), fixing the protective tube (3) in down folded position;
  K) the hinge (5) is a so-called ribbon hinge, below which there is a unfolding fixing cam (13), formed in such a way, that it ensures temporary engagement to the coupling opening (15) formed in the protective tube (3) fixing the protective tube (3) in down folded position;
  L) the hinge (5) is such a ribbon hinge, that is made in open position;
  M) there is a tearing element (12) confirming the first use, formed between the edges of the slit (7) of the protective tube (3) and the appendix (4);
  N) the needle protector (1) is provided with a further valve realized with compressible closing elements (18), joining the edges of the slit (7) compressing and closing it;
  O) the needle protector (1) is provided with a further valve, realized in the form of a protective cap (14), which connects to the protruding part (9) with the help of fixing elements (17) preventing backward movement in pushed position movable in axial direction;
  P) the raw material of the whole needle protector (1) is flexible plastic; and/or
  Q) the needle (2) together with the needle protector (1) is provided with sterilizable packaging.

18. A needle protector of claim 17, wherein condition A) has been met.

19. A needle protector of claim 17, wherein one of conditions F) or G) has been met.

20. A needle protector of claim 17, wherein at least three of conditions A)-Q) have been met.

* * * * *